United States Patent
Yukuhiro et al.

(10) Patent No.: US 11,590,106 B2
(45) Date of Patent: Feb. 28, 2023

(54) ASENAPINE-CONTAINING ADHESIVE PATCH

(71) Applicant: Hisamitsu Pharmaceutical Co., Inc., Tosu (JP)

(72) Inventors: Masaki Yukuhiro, Tsukuba (JP); Yuka Takagi, Tsukuba (JP); Yasunari Michinaka, Tsukuba (JP)

(73) Assignee: Hisamitsu Pharmaceutical Co., Inc., Saga (JP)

( * ) Notice: Subject to any disclaimer, the term of this patent is extended or adjusted under 35 U.S.C. 154(b) by 7 days.

(21) Appl. No.: 17/281,623

(22) PCT Filed: Sep. 25, 2019

(86) PCT No.: PCT/JP2019/037586
§ 371 (c)(1),
(2) Date: Mar. 31, 2021

(87) PCT Pub. No.: WO2020/071207
PCT Pub. Date: Apr. 9, 2020

(65) Prior Publication Data
US 2021/0393587 A1    Dec. 23, 2021

(30) Foreign Application Priority Data
Oct. 1, 2018   (JP) .............................. JP2018-186876

(51) Int. Cl.
| | |
|---|---|
| *A61K 31/407* | (2006.01) |
| *A61K 9/70* | (2006.01) |
| *A61K 47/02* | (2006.01) |
| *A61K 47/12* | (2006.01) |
| *A61K 47/32* | (2006.01) |

(52) U.S. Cl.
CPC .......... *A61K 31/407* (2013.01); *A61K 9/7069* (2013.01); *A61K 47/02* (2013.01); *A61K 47/12* (2013.01); *A61K 47/32* (2013.01)

(58) Field of Classification Search
CPC .... A61K 31/407; A61K 9/7069; A61K 47/02; A61K 47/12; A61K 47/32; A61K 47/10; A61P 25/18
See application file for complete search history.

(56) References Cited

U.S. PATENT DOCUMENTS

| | | | |
|---|---|---|---|
| 2013/0315976 A1 | 11/2013 | Okada et al. | |
| 2015/0164862 A1* | 6/2015 | Suzuki ................. | A61K 31/55 424/443 |
| 2015/0202183 A1 | 7/2015 | Suzuki et al. | |
| 2015/0231250 A1 | 8/2015 | Sonobe et al. | |
| 2018/0193283 A1 | 7/2018 | Mohr et al. | |
| 2018/0207108 A1 | 7/2018 | Sonobe et al. | |
| 2019/0000775 A1 | 1/2019 | Yasukochi et al. | |

FOREIGN PATENT DOCUMENTS

| | | |
|---|---|---|
| CN | 103338788 A | 10/2013 |
| WO | WO 2010/127674 A1 | 11/2010 |
| WO | WO 2014/017593 A1 | 1/2014 |
| WO | WO 2014/017594 A1 | 1/2014 |
| WO | WO 2014/017595 A1 | 1/2014 |
| WO | WO 2017/018321 A1 | 2/2017 |
| WO | WO 2017/018322 A1 | 2/2017 |
| WO | WO 2017/131034 A1 | 8/2017 |
| WO | WO 2018/115010 A1 | 6/2018 |
| WO | WO 2019/002204 A1 | 1/2019 |

OTHER PUBLICATIONS

Yasukochi et al. (WO2017018322A1 Machine Translation) (Year: 2017).*
U.S. Appl. No. 17/281,621, filed Mar. 31, 2021, Yukuhiro et al.
PCT/JP2019/037586, Dec. 10, 2019, Translation of the International Search Report and Written Opinion.

* cited by examiner

*Primary Examiner* — Robert A Wax
*Assistant Examiner* — Quanglong N Truong
(74) *Attorney, Agent, or Firm* — Wolf, Greenfield & Sacks, P.C.

(57) ABSTRACT

An object of the present invention is to provide an asenapine-containing patch having excellent sustained-release properties while enhancing skin permeability by using a silicone-based pressure-sensitive adhesive base. The present invention relates to a patch having a support and a pressure-sensitive adhesive layer, wherein the pressure-sensitive adhesive layer comprises asenapine and/or a pharmaceutically acceptable salt thereof, a silicone-based pressure-sensitive adhesive base and a release control agent, and the ratio of the maximum skin permeation rate of asenapine to the minimum skin permeation rate from the time when the maximum skin permeation rate is reached to 24 hours is less than 1.62.

8 Claims, No Drawings

ASENAPINE-CONTAINING ADHESIVE PATCH

RELATED APPLICATION

This application is a national stage filing under 35 U.S.C. § 371 of International Patent Application Serial No. PCT/JP2019/037586, filed Sep. 25, 2019, the content of which is incorporated by reference herein in its entirety.

TECHNICAL FIELD

The present invention relates to a patch containing asenapine in the pressure-sensitive adhesive layer and a method for producing the same.

BACKGROUND ART

Asenapine is known as a therapeutic agent for central nervous system diseases such as schizophrenia, and sublingual tablets (Sycrest® sublingual tablets and Saphris® sublingual tablets) are commercially available. At present, asenapine is not commercially available in dosage forms other than sublingual tablets.

Asenapine-containing patches are described in, for example, Patent documents 1 to 5, and all of them have been studied mainly for patches using rubber-based pressure-sensitive adhesive bases and acrylic-based pressure-sensitive adhesive bases.

An asenapine-containing patch in which a polysiloxane pressure-sensitive adhesive and a polyacrylate pressure-sensitive adhesive are combined is described in, for example, Patent document 6, in particular Example 14.

CITATION LIST

Patent Document

[Patent document 1] WO No. 2014/017593
[Patent document 2] WO No. 2014/017594
[Patent document 3] WO No. 2014/017595
[Patent document 4] WO No. 2017/018321
[Patent document 5] WO No. 2017/018322
[Patent document 6] WO No. 2010/127674

SUMMARY OF INVENTION

Problems to be Solved by the Invention

During examination of patches containing asenapine, present inventors have come to know that, regarding patches using asenapine and a silicone-based pressure-sensitive adhesive base, while they tend to have higher skin permeability than patches using a rubber-based pressure-sensitive adhesive base, their immediate effect tends to be enhanced; therefore, a patch with excellent sustained-release properties is required.

Thus, an object of the present invention is to provide an asenapine-containing patch having high skin permeability and excellent sustained-release properties by using a silicone-based pressure-sensitive adhesive base.

Means for Solving Problems

The present inventors have conducted extensive research to solve such a problem, and found that, by adjusting the ratio of the maximum skin permeation rate of asenapine to the minimum skin permeation rate from the time when the maximum skin permeation rate is reached to 24 hours to a predetermined range, the skin permeability of a patch containing asenapine and a silicone-based pressure-sensitive adhesive can be enhanced, and it is possible to provide an asenapine-containing patch having excellent sustained-release properties; as a result of further research, the present inventors have completed the present invention. That is, the present invention relates to the following.

[1] A patch comprising a support and a pressure-sensitive adhesive layer,
wherein the pressure-sensitive adhesive layer comprises asenapine and/or a pharmaceutically acceptable salt thereof, a silicone-based pressure-sensitive adhesive base, and a release control agent, and
wherein the ratio of the maximum skin permeation rate of asenapine to the minimum skin permeation rate from the time when the maximum skin permeation rate is reached to 24 hours is less than 1.62.
[2] The patch according to [1], wherein the silicone-based pressure-sensitive adhesive base is an amine-compatible silicone-based pressure-sensitive adhesive base.
[3] The patch according to [1] or [2], wherein the silicone-based pressure-sensitive adhesive base comprises at least one selected from the group consisting of high-tack amine-compatible silicone-based pressure-sensitive adhesive bases, medium-tack amine-compatible silicone-based pressure-sensitive adhesive bases and low-tack amine-compatible silicone-based pressure-sensitive adhesive bases.
[4] The patch according to [3], wherein the silicone-based pressure-sensitive adhesive base comprises a high-tack amine-compatible silicone-based pressure-sensitive adhesive base and a medium-tack amine-compatible silicone-based pressure-sensitive adhesive base.
[5] The patch according to any one of [1] to [4], wherein the content of the silicone-based pressure-sensitive adhesive base in the pressure-sensitive adhesive layer is 72 mass % to 96 mass %.
[6] The patch according to any one of [1] to [5], wherein the release control agent is at least one selected from the group consisting of oleic acid, magnesium aluminometasilicate, methacrylic acid-methacrylate copolymers, N-methyl-2-pyrrolidone, and (meth)acrylate (co)polymers.
[7] The patch according to [6], wherein the release control agent is at least one selected from the group consisting of oleic acid and magnesium aluminometasilicate, and wherein the content in the pressure-sensitive adhesive layer is 2.5 mass % to 7.5 mass %.
[8] The patch according to [6], wherein the release control agent is at least one selected from the group consisting of methacrylic acid-methacrylate copolymers and N-methyl-2-pyrrolidone, and wherein the content in the pressure-sensitive adhesive layer is 1.0 mass % to 5.0 mass %.
[9] The patch according to [6], wherein the release control agent is at least one selected from the group consisting of (meth)acrylate (co)polymers, and wherein the content in the pressure-sensitive adhesive layer is 12 mass % to 25.0 mass %.

Advantageous Effects of Invention

According to the present invention, high skin permeability and excellent sustained-release properties can be achieved in a patch containing a silicone-based pressure-sensitive adhesive layer that comprises asenapine and/or a pharmaceutically acceptable salt thereof. Therefore, it is possible to provide a patch that can be designed with a relatively long application time.

Embodiments for Carrying Out Invention

The patch of the present invention comprises, for example, a support and a pressure-sensitive adhesive layer laminated on the support.

The support may be any one that can maintain the shape of the patch, in particular, of the pressure-sensitive adhesive layer. Examples of a material of the support include polyamides such as polyethylene, polypropylene, polybutadiene, ethylene-vinyl chloride copolymer, polyvinyl chloride, and nylon (trade name); synthetic resins such as polyester, cellulose derivatives, and polyurethane. The properties and condition of the support include, for example, films, sheets, sheet-like porous materials, sheet-like foams, fabrics such as woven fabrics, knitted fabrics, non-woven fabrics, and laminates thereof. The thickness of the support is not particularly limited, and is usually preferably about 2 to 3000 μm.

The pressure-sensitive adhesive layer comprises asenapine and/or a pharmaceutically acceptable salt thereof, a silicone-based pressure-sensitive adhesive base and a release control agent. Furthermore, the patch of the present invention may contain, in addition to asenapine and/or a pharmaceutically acceptable salt thereof, a silicone-based pressure-sensitive adhesive base and a release control agent, if necessary, other additives such as antioxidants, tackifier resins, plasticizers, absorption promoters, solubilizers, cross-linking agents, antiseptics, fillers, preservatives, fragrances, etc.

The asenapine of the present invention is a compound also called trans-5-chloro-2-methyl-2,3,3a,12b-tetrahydro-1H-dibenz[2, 3:6,7]oxepino[4,5-c]pyrrole. Asenapine has a plurality of optical isomers, and any of the optical isomers can be used, and a mixture of optical isomers such as racemates may be used. The acid added to asenapine is not particularly limited as long as it is a pharmaceutically acceptable acid. The acid addition salt of asenapine may be anhydrous or hydrated.

Examples of the acid in the acid addition salt of asenapine include hydrochloric acid, hydrobromic acid, hydroiodic acid, phosphoric acid, acetic acid, propionic acid, glycolic acid, maleic acid, malonic acid, succinic acid, tartaric acid, citric acid, ascorbic acid, salicylic acid, benzoic acid, etc. For example, asenapine maleate is commercially available as sublingual tablets (Sycrest® sublingual tablets and Saphris® sublingual tablets).

The desalting agent may be any one as long as it can convert the acid addition salt of asenapine into an asenapine free base by a salt exchange reaction with the acid addition salt of asenapine. That is, the desalting agent means a component that converts an acid addition salt of asenapine into an asenapine free base. Examples of desalting agent include alkali metal hydroxides, alkali metal salts, alkaline earth metal hydroxides, alkaline earth metal salts, low molecular weight amines, etc. Examples of alkali metal hydroxide include lithium hydroxide, sodium hydroxide, potassium hydroxide, and one of these may be used alone, and two or more may be used in combination. Examples of alkali metal salt include sodium carbonate, potassium carbonate, sodium hydrogen carbonate, trisodium phosphate, disodium hydrogen phosphate, sodium dihydrogen phosphate, tripotassium phosphate, dipotassium hydrogen phosphate, potassium dihydrogen phosphate, sodium lactate, sodium citrate, disodium tartrate, sodium hydrogen tartrate, sodium oleate, etc. The low molecular weight amine is an amine having a molecular weight of 30 to 300, and examples thereof include monoethanolamine, diethanolamine, triethanolamine, isopropanolamine, and diisopropanolamine, etc. The desalting agent may be selected in consideration of pKa of the acid added to asenapine. When the desalting agent is sodium hydroxide or sodium acetate, the drug is less degraded during production of the patch.

The content of asenapine and/or a pharmaceutically acceptable salt thereof can be appropriately set by those skilled in the art, and it is preferably 0.5 to 30 mass % in terms of asenapine free form based on the total amount of the pressure-sensitive adhesive layer, and it is more preferably 1 to 20 mass %, furthermore preferably 1.5 to 12 mass %, and particularly preferably 2 to 10 mass %.

In the patch of the present invention, the ratio of the maximum skin permeation rate of asenapine to the minimum skin permeation rate from the time when the maximum skin permeation rate is reached to 24 hours is preferably less than 1.62, more preferably 1 to 1.47, and furthermore preferably 1 to 1.43. By setting the ratio of the maximum skin permeation rate of asenapine to the minimum skin permeation rate from the time when the maximum skin permeation rate is reached to 24 hours to less than 1.62, sufficient sustained-release properties can be ensured Here, the "maximum skin permeation rate" is a maximum value of the permeation amounts of asenapine per unit area of the skin-attached surface of the adhesive layer which are converted to the values per unit time, that is, it means the maximum value of the skin permeation rate of the drug within the measurement time. The "minimum skin permeation rate from the time when the maximum skin permeation rate is reached to 24 hours" means the minimum value of the permeation amounts of asenapine per unit area of the skin-attached surface of the adhesive layer from the time when the maximum skin permeation rate is reached to 24 hours which are converted to the values per unit time.

The silicone-based pressure-sensitive adhesive base is a compound having an organopolysiloxane skeleton.

Examples of the silicone-based pressure-sensitive adhesive base include a mixture of silicone rubber and silicone resin, or a dehydration-condensation product thereof in the presence of an alkaline catalyst, etc.; and a condensation product of silicone rubber and silicone resin is preferable.

The silicone rubber constituting the silicone-based pressure-sensitive adhesive base is, for example, a long-chain polymer having hydroxy groups at both ends of polyorganosiloxane. As the organosiloxane unit of the silicone rubber, a silicone rubber containing dimethylsiloxane as a main component is preferable.

The silicone resin constituting the silicone-based pressure-sensitive adhesive base is not particularly limited, and a silicate resin having a three-dimensional structure is preferable.

Examples of the silicone-based pressure-sensitive adhesive base include dimethylpolysiloxane, polymethylvinylsiloxane, and polymethylphenylsiloxane. Specific silicone-based pressure-sensitive adhesive bases include, for example, MD series (Dow Corning Corp.) such as MD7-4502 Silicone Adhesive, MD7-4602 Silicone Adhesive; BIO-PSA series (Dow Corning Corp.) such as BIO-PSA® 7-4301 Silicone Adhesive, BIO-PSA® 7-4302 Silicone Adhesive, BIO-PSA® 7-4201 Silicone Adhesive, BIO-PSA® 7-4202 Silicone Adhesive, BIO-PSA® 7-4101 Silicone Adhesive, BIO-PSA® 7-4102 Silicone Adhesive, BIO-PSA® 7-4601 Silicone Adhesive, BIO-PSA® 7-4602 Silicone Adhesive, BIO-PSA® 7-4501 Silicone Adhesive, BIO-PSA® 7-4502 Silicone Adhesive, BIO-PSA®7-4401

Silicone Adhesive, BIO-PSA® 7-4402 Silicone Adhesive, BIO-PSA® 7-4100 Silicone Adhesive, BIO-PSA® 7-4200 Silicone Adhesive, BIO-PSA® 7-4300 Silicone Adhesive, BIO-PSA® 7-4400 Silicone Adhesive, BIO-PSA® 7-4500 Silicone Adhesive, BIO-PSA® 7-4600 Silicone Adhesive; Dow Corning® 7-9800A, Dow Corning® 7-9800B, Dow Corning® 7-9700A, Dow Corning® 7-9700B.

The silicone-based pressure-sensitive adhesive base of the present invention is preferably an amine-compatible silicone-based pressure-sensitive adhesive base. The amine-compatible silicone-based pressure-sensitive adhesive base is a silicone-based pressure-sensitive adhesive base wherein, for example, after condensing polydimethylsiloxane and silicone resin, silanol groups that remain upon condensation by trimethylsilylation, etc. are blocked by trimethylsilyl groups, etc., thereby suppressing the remaining silanol concentration.

In addition, the silicone-based pressure-sensitive adhesive base can be roughly classified into three types: high tack, medium tack, and low tack, depending on the tack property; in the present invention, these can be appropriately combined and used.

According to JIS K6800-1985 or ISO6354, tack refers to the property of a pressure-sensitive adhesive that can form a bond immediately after contacting the surface of a material to be adhered with a very light force.

The high-tack amine-compatible silicone-based pressure-sensitive adhesive base in the present invention has a weight ratio of silicone resin to silicone rubber of approximately 52.5:47.5 (w/w) to 57.5:42.5 (w/w), and it is preferably an amine-compatible silicone-based pressure-sensitive adhesive base having 55:45 (w/w). Examples of high-tack amine-compatible silicone-based pressure-sensitive adhesive base include BIO-PSA® 7-4302 Silicone Adhesive and BIO-PSA® 7-4301 Silicone Adhesive.

The medium-tack amine-compatible silicone-based pressure-sensitive adhesive base in the present invention has a weight ratio of silicone resin to silicone rubber of approximately 57.5:42.5 (w/w) to 62.5:37.5 (w/w), and it is preferably an amine-compatible silicone-based pressure-sensitive adhesive base having 60:40 (w/w). Examples of the medium-tack amine-compatible silicone-based pressure-sensitive adhesive base include BIO-PSA® 7-4202 Silicone Adhesive and BIO-PSA® 7-4201 Silicone Adhesive.

The low-tack amine-compatible silicone-based pressure-sensitive adhesive base in the present invention has a weight ratio of silicone resin to silicone rubber of approximately 62.5:37.5 (w/w) to 67.5:32.5 (w/w), and it is preferably an amine-compatible silicone-based pressure-sensitive adhesive base having 65:35 (w/w). Examples of the low-tack amine-compatible silicone-based pressure-sensitive adhesive base include BIO-PSA® 7-4102 Silicone Adhesive and BIO-PSA® 7-4101 Silicone Adhesive.

In one embodiment, the present invention contains a high-tack amine-compatible silicone-based pressure-sensitive adhesive base and a medium-tack amine-compatible silicone-based pressure-sensitive adhesive base. The mass ratio of the high-tack amine-compatible silicone-based pressure-sensitive adhesive base to the medium-tack amine-compatible silicone-based pressure-sensitive adhesive base can be appropriately determined, and it is preferably 90:10 to 10:90, more preferably 87.5:12.5 to 12.5:87.5, and even more preferably 75:25 to 25:75.

In one embodiment, the present invention contains a high-tack amine-compatible silicone-based pressure-sensitive adhesive base and a low-tack amine-compatible silicone-based pressure-sensitive adhesive base. The mass ratio of the high-tack amine-compatible silicone-based pressure-sensitive adhesive base to the low-tack amine-compatible silicone-based pressure-sensitive adhesive base can be appropriately determined, and is preferably 90:10 to 30:70, more preferably 90:10 to 50:50, further preferably 87.5:12.5 to 50:50, and even more preferably 75:25 to 50:50.

In the patch of the present invention, the content of the silicone-based pressure-sensitive adhesive base in the pressure-sensitive adhesive layer is preferably 60 mass % to 98 mass %, more preferably 66 mass % to 97 mass %, and even more preferably 72 mass % to 96 mass %.

The patch of the present invention contains a release control agent in the pressure-sensitive adhesive layer.

The release control agent is not particularly limited as long as it can control the release of asenapine and/or a pharmaceutically acceptable salt thereof in the silicone-based pressure-sensitive adhesive base, and preferred examples thereof include oleic acid, magnesium aluminometasilicate, methacrylic acid-methacrylate (co)polymers, N-methyl-2-pyrrolidone, and (meth)acrylate (co)polymers. Therefore, the release control agent of the present invention is at least one selected from the group consisting of oleic acid, magnesium aluminometasilicate, methacrylic acid-methacrylate (co)polymers, N-methyl-2-pyrrolidone, and (meth)acrylate (co)polymers, and particularly preferably it is at least one selected from the group consisting of oleic acid, magnesium aluminometasilicate, methacrylic acid-methacrylate (co)polymers, and (meth)acrylate (co)polymers.

The content of the release control agent in the pressure-sensitive adhesive layer can be appropriately selected depending on the type thereof, and it is preferably about 1.0 mass % to 25.0 mass %.

When the release control agent is at least one selected from the group consisting of oleic acid and magnesium aluminometasilicate, the content in the pressure-sensitive adhesive layer is preferably 1.0 mass % to 10.0 mass %, particularly preferably 2.5 mass % to 7.5 mass %.

When the release control agent is at least one selected from the group consisting of a methacrylic acid-methacrylate (co)polymer and N-methyl-2-pyrrolidone, the content in the pressure-sensitive adhesive layer is preferably 1.0 mass % to 10.0 mass %, more preferably 1.0 mass % to 5.0 mass %, and particularly preferably 1.0 mass % to 3.0 mass %.

When the release control agent is at least one selected from the group consisting of (meth)acrylate (co) polymers, the content in the pressure-sensitive adhesive layer is preferably 1.0 mass % to 25.0 mass %, particularly preferably 12 mass % to 25.0 mass %.

Examples of the methacrylic acid-methacrylate (co)polymer include poly(methacrylic acid-co-methyl methacrylate) and poly(methacrylic acid-co-ethyl methacrylate), etc. Specific examples thereof include Eudragit® L100 (Evonik Industries).

Examples of the (meth)acrylate (co) polymer include (co)polymers of one or more alkyl (meth)acrylates. Examples of the alkyl (meth)acrylate include butyl (meth)acrylate, isobutyl (meth)acrylate, hexyl (meth)acrylate, octyl (meth)acrylate, 2-ethylhexyl (meth)acrylate, and decyl (meth)acrylate, etc. Here, (meth)acrylate means acrylate or methacrylate.

The (meth)acrylate (co)polymer may be a (co)polymer formed from alkyl (meth)acrylate (main monomer) and a comonomer. The comonomer may be a component that can be copolymerized with alkyl (meth)acrylate. Examples of the comonomer include hydroxyalkyl (meth)acrylate, ethylene, propylene, styrene, vinyl acetate, N-vinylpyrrolidone, and (meth)acrylic acid amide. The comonomer may be used alone or in combination of two or more.

Specific examples of (meth)acrylate (co)polymer include DURO-TAK® 87-900A, DURO-TAK® 87-2510, DURO-TAK® 87-235A, DURO-TAK®87-4287, DURO-TAK®87-2287, DURO-TAK®87-2516 (trade name, Henkel Corporation) and the like.

Examples of antioxidants include tocopherols and their ester derivatives, ascorbic acid, ascorbyl stearate, nordihitolog ayaretic acid, dibutylhydroxytoluene (BHT), butylhydroxyanisole (BHA), citric acid, 2-mercaptobenzimidazole, and ethylenediamine tetraacetic acid. The antioxidant may be used alone or in combination of two or more.

The plasticizer may be any one that imparts flexibility to the pressure-sensitive adhesive layer. Examples of the plasticizer include mineral oils (e.g., paraffin oil, naphthenic oil, aromatic oils), animal oils (e.g., squalane, squalene), vegetable oils (e.g., olive oil, camellia oil, castor oil, tall oil, peanut oil), silicone oil, dibasic acid esters (e.g., dibutylphthalate, dioctylphthalate), liquid rubbers (e.g., liquid polybutene, liquid polyisoprene), liquid fatty acid esters (e.g., isopropyl myristate, hexyl laurate, diethyl sebacate, diisopropyl sebacate), polyhydric alcohols (e.g., diethylene glycol, polyethylene glycol, propylene glycol, dipropylene glycol), triacetin, triethyl citrate, crotamitone and the like. The plasticizer may be used alone or in combination of two or more.

The absorption promoter is a component that regulates the skin permeability of asenapine and/or its pharmaceutically acceptable salt. The absorption promoter is not particularly limited as long as it is a compound that has been conventionally recognized to have an absorption-promoting effect on the skin. Examples thereof include aliphatic alcohols such as isostearyl alcohol, fatty acids such as capric acid, fatty acid derivatives such as propylene glycol monolaurate, isopropyl myristate, isopropyl palmitate and diethanolamide laurate, and glycols such as propylene glycol and polyethylene glycol. The absorption promoter may be used alone or in combination of two or more.

The cross-linking agent is not particularly limited, and preferred examples include thermosetting resins such as amino resins, phenol resins, epoxy resins, alkyd resins, and unsaturated polyesters; isocyanate compounds, blocked isocyanate compounds, organic cross-linking agents, inorganic cross-linking agents such as metals and metal compounds, and the like.

The antiseptic is not particularly limited, and preferable examples include ethyl paraoxybenzoate, propyl paraoxybenzoate, butyl paraoxybenzoate and the like. The filler is not particularly limited, and preferred examples include calcium carbonate, magnesium carbonate, silicates (aluminum silicate, calcium silicate, magnesium silicate, etc.), and cellulose derivatives (hydroxypropyl cellulose, hydroxypropyl methyl cellulose, carboxymethyl cellulose, etc.).

Examples of the filler include aluminum hydroxide, calcium carbonate, magnesium carbonate, silicates (e.g., aluminum silicate, magnesium silicate), silicic acid, barium sulfate, calcium sulfate, calcium zincate, zinc oxide, titanium oxide, etc.

Examples of the preservative include disodium edetate, tetrasodium edetate, ethyl paraoxybenzoate, propyl paraoxybenzoate, butyl paraoxybenzoate, etc. The preservative may be used alone or in combination of two or more.

In one embodiment of the present invention, the mass of the pressure-sensitive adhesive layer is preferably 30 to 200 g/m$^2$, more preferably 30 to 150 g/m$^2$, and furthermore preferably 30 to 130 g/m$^2$. When the mass is too small, problems such as poor adhesiveness and difficulty in production may occur, and when the mass is too large, cold flow tends to occur easily and the physical properties may be deteriorated.

Cold flow is a phenomenon in which a pressure-sensitive adhesive flows/deforms at room temperature during storage or application. When cold flow occurs, the pressure-sensitive adhesive layer protrudes from the side surface of a patch on which a support and the pressure-sensitive adhesive layer are laminated, to the outside beyond the range covered by the support, and the shape of the patch cannot be maintained; and the following problems occur: for example, the protruding part of the pressure-sensitive adhesive layer adheres to the inner surface of the packaging material of the patch, which affects the temporal stability of asenapine, and the skin permeability decreases with a decrease in asenapine content, and it becomes difficult to remove the patch from the packaging material.

The patch may further comprise a release liner. The release liner is laminated on the pressure-sensitive adhesive layer on the surface opposite to the support side. When a release liner is provided, there is a tendency to reduce the adhesion of dust and the like to the pressure-sensitive adhesive layer during storage.

The material of the release liner is not particularly limited, and a film generally known to those skilled in the art can be used. Examples of the material of the release liner include polyesters such as polyethylene terephthalate and polyethylene naphthalate; polyolefins such as polyethylene and polypropylene; films such as polyvinyl chloride and polyvinylidene chloride; laminated films of high-quality paper and polyolefin; films such as Nylon® and aluminum, and the like. As the material of the release liner, polypropylene or polyethylene terephthalate is preferable.

Next, an example of the method for producing the patch of the present invention will be described.

First, a mixture for forming a pressure-sensitive adhesive layer is prepared. The mixture for forming a pressure-sensitive adhesive layer is obtained by dissolving or dispersing the above-mentioned asenapine and/or a pharmaceutically acceptable salt thereof, a silicone-based pressure-sensitive adhesive base, and other components in a solvent using a mixer.

As the solvent, toluene, hexane, ethyl acetate, cyclohexane, heptane, butyl acetate, ethanol, methanol, xylene, isopropanol, etc. can be used. These can be appropriately selected depending on the components to be dissolved or dispersed, and one type can be used alone or two or more types can be mixed and used in combination.

Next, the obtained mixture for forming the pressure-sensitive adhesive layer is spread directly on a support and dried to form the pressure-sensitive adhesive layer, and then a release liner for protecting the pressure-sensitive adhesive layer is adhered on the pressure-sensitive adhesive layer; alternatively, the obtained mixture for forming the pressure-sensitive adhesive layer is spread on a release-treated paper or film and dried to form a pressure-sensitive adhesive layer, then a support is placed on it to pressure-bond the pressure-sensitive adhesive layer onto the support; thus a patch is obtained.

EXAMPLES

Example 1. Preparation of Patch

Patches 1 to 20 consisting of the bases, drug concentration, and additives shown in Table 1 were prepared. Here, asenapine (free form) of 3.2 mass % with respect to the pressure-sensitive adhesive layer was added to each patch, and the mass of the pressure-sensitive adhesive was 100 g/m$^2$ (set value).

TABLE 1

| Patch | Base | Drug concentration | Additive | Jmax/Jmin (up to 24 h after Tmax) |
|---|---|---|---|---|
| 1 | 94.3% PSA7-4202 | 3.2% (free form) | 2.5% Oleic acid | 1.224 |
| 2 | 94.3% PSA7-4202 | 3.2% (free form) | 2.5% Mg aluminometasilicate | 1.427 |
| 3 | 91.8% PSA7-4202 | 3.2% (free form) | 5.0% Mg aluminometasilicate | 1.320 |
| 4 | 89.3% PSA7-4202 | 3.2% (free form) | 7.5% Mg aluminometasilicate | 1.400 |
| 5 | 95.8% PSA7-4202 | 3.2% (free form) | 1.0% L-100 | 1.381 |
| 6 | 93.8% PSA7-4202 | 3.2% (free form) | 3.0% L-100 | 1.403 |
| 7 | 91.8% PSA7-4202 | 3.2% (free form) | 5.0% L-100 | 1.337 |
| 8 | 95.8% PSA7-4202 | 3.2% (free form) | 1.0% NMP | 1.469 |
| 9 | 93.8% PSA7-4202 | 3.2% (free form) | 3.0% NMP | 1.600 |
| 10 | 91.8% PSA7-4202 | 3.2% (free form) | 5.0% NMP | 1.615 |
| 11 | 84.7% PSA7-4202 | 3.2% (free form) | 12.1% 900A | 1.296 |
| 12 | 72.6% PSA7-4202 | 3.2% (free form) | 24.2% 900A | 1.126 |
| 13 | 84.7% PSA7-4202 | 3.2% (free form) | 12.1% 2510 | 1.236 |
| 14 | 72.6% PSA7-4202 | 3.2% (free form) | 24.2% 2510 | 1.067 |
| 15 | 94.3% PSA7-4202 | 3.2% (free form) | 2.5% Oleyl alcohol | 1.823 |
| 16 | 94.3% PSA7-4202 | 3.2% (free form) | 2.5% Propylene glycol | 1.638 |
| 17 | 94.3% PSA7-4202 | 3.2% (free form) | 2.5% Myristyl alcohol | 1.718 |
| 18 | 96.8% PSA7-4102 | 3.2% (free form) | None | 1.631 |
| 19 | 96.8% PSA7-4202 | 3.2% (free form) | None | 1.812 |
| 20 | 96.8% PSA7-4302 | 3.2% (free form) | None | 1.709 |

The meanings of the abbreviations in Table 1 are as follows.
<Base>
PSA7-4102: BIO-PSA® 7-4102 Silicone Adhesive (Dow Corning Corp.)
PSA7-4202: BIO-PSA® 7-4202 Silicone Adhesive (Dow Corning Corp.)
PSA7-4302: BIO-PSA® 7-4302 Silicone Adhesive (Dow Corning Corp.)
<Additive>
L-100: Eudragit® L100 (Evonik Industries)
NMP: N-methyl-2-pyrrolidone
900A: DURO-TAK® 87-900A (Henkel Corporation)
2510: DURO-TAK® 87-2510 (Henkel Corporation)

Example 2. In Vitro Skin Permeation Test

A 2.5-cm$^2$ patch was applied to the stratum corneum side of a skin removed from a hairless mouse, and the skin was attached to a flow-through type diffusion cell kept at 32° C. such that the dermis side was on the receptor tank side. In the test, liquid was collected every 4 hours while replacing the phosphate buffered saline in the receptor tank. The drug concentration in the obtained liquid was measured by high performance liquid chromatography. The amount of permeated drug at each time was calculated from the concentration value, and the skin permeation rate of the drug was calculated, then the maximum skin permeation rate Jmax (µg/h/cm$^2$) was determined.

Similarly, the minimum skin permeation rate (Jmin (µg/h/cm$^2$)) from the time when the maximum skin permeation rate was reached (Tmax) to 24 hours was determined.

The ratio of the maximum skin permeation rate to the minimum skin permeation rate from the time when the maximum skin permeation rate was reached to 24 hours (Jmax/Jmin (up to 24 hours after Tmax)) was calculated; the results are shown in Table 1.

As an additive, when oleic acid (patch 1), magnesium aluminometasilicate (patches 2 to 4), Eudragit® L100 (patches 5 to 7), N-methyl-2-pyrrolidone (patches 8 to 10), DURO-TAK® 87-900A (patches 11 and 12), and DURO-TAK® 87-2510 (patches 13 and 14) were used, Jmax/Jmin (up to 24 hours after Tmax) values were less than 1.62; and for the above-mentioned patches 1 to 14, Jmax/Jmin (up to 24 hours after Tmax) values were less than 1.43 except for N-methyl-2-pyrrolidone (patches 8 to 10).

The invention claimed is:
1. A patch comprising a support and a pressure-sensitive adhesive layer,
wherein the pressure-sensitive adhesive layer comprises asenapine and/or a pharmaceutically acceptable salt thereof, a silicone-based pressure-sensitive adhesive base, and a release control agent selected from the group consisting of oleic acid, magnesium aluminometasilicate, methacrylic acid-methacrylate copolymers, N-methyl-2-pyrrolidone, and (meth)acrylate (co)polymers, and
wherein the ratio of the maximum skin permeation rate of asenapine to the minimum skin permeation rate from the time when the maximum skin permeation rate is reached to 24 hours is less than 1.62.
2. The patch according to claim 1, wherein the silicone-based pressure-sensitive adhesive base is an amine-compatible silicone-based pressure-sensitive adhesive base.

3. The patch according to claim 1, wherein the silicone-based pressure-sensitive adhesive base comprises at least one selected from the group consisting of high-tack amine-compatible silicone-based pressure-sensitive adhesive bases, medium-tack amine-compatible silicone-based pressure-sensitive adhesive bases and low-tack amine-compatible silicone-based pressure-sensitive adhesive bases.

4. The patch according to claim 3, wherein the silicone-based pressure-sensitive adhesive base comprises a high-tack amine-compatible silicone-based pressure-sensitive adhesive base and a medium-tack amine-compatible silicone-based pressure-sensitive adhesive base.

5. The patch according to claim 1, wherein the content of the silicone-based pressure-sensitive adhesive base in the pressure-sensitive adhesive layer is 72 mass % to 96 mass %.

6. The patch according to claim 1, wherein the release control agent is at least one selected from the group consisting of oleic acid and magnesium aluminometasilicate, and wherein the content in the pressure-sensitive adhesive layer is 2.5 mass % to 7.5 mass %.

7. The patch according to claim 1, wherein the release control agent is at least one selected from the group consisting of methacrylic acid-methacrylate copolymers and N-methyl-2-pyrrolidone, and wherein the content in the pressure-sensitive adhesive layer is 1.0 mass % to 5.0 mass %.

8. The patch according to claim 1, wherein the release control agent is at least one selected from the group consisting of (meth)acrylate (co)polymers, and wherein the content in the pressure-sensitive adhesive layer is 12 mass % to 25.0 mass %.

* * * * *